United States Patent
Satoh et al.

(10) Patent No.: US 10,846,861 B2
(45) Date of Patent: Nov. 24, 2020

(54) IMAGE PROCESSOR, IMAGE PROCESSING METHOD, PROGRAM FOR IMAGE PROCESSING, AND MAGNETIC RESONANCE IMAGING APPARATUS

(71) Applicant: Hitachi, Ltd., Chiyoda-ku (JP)

(72) Inventors: Ryota Satoh, Tokyo (JP); Kohsuke Kudo, Hokkaido (JP); Toru Shirai, Tokyo (JP); Yasuo Kawata, Tokyo (JP)

(73) Assignee: HITACHI, LTD., Tokyo (JP)

( * ) Notice: Subject to any disclaimer, the term of this patent is extended or adjusted under 35 U.S.C. 154(b) by 22 days.

(21) Appl. No.: 16/384,387

(22) Filed: Apr. 15, 2019

(65) Prior Publication Data

US 2020/0074635 A1 Mar. 5, 2020

(30) Foreign Application Priority Data

Aug. 29, 2018 (JP) .................................. 2018-160616

(51) Int. Cl.
    *G06K 9/00*         (2006.01)
    *G06T 7/11*         (2017.01)
    (Continued)

(52) U.S. Cl.
    CPC .............. *G06T 7/11* (2017.01); *A61B 5/0042* (2013.01); *A61B 5/055* (2013.01); *G01R 33/443* (2013.01);
    (Continued)

(58) Field of Classification Search
    CPC ... G06T 7/11; G06T 7/00; G06T 7/174; G06T 7/62; G06T 7/0012; G06T 2207/10088;
    (Continued)

(56) References Cited

U.S. PATENT DOCUMENTS

| 9,285,449 B2 * | 3/2016 | Liu | ...................... G01R 33/443 |
| 2004/0218794 A1 * | 11/2004 | Kao | .......................... G06T 7/11 |
| | | | 382/128 |

(Continued)

FOREIGN PATENT DOCUMENTS

WO     WO-2017056996 A1 *     4/2017     ............. G01R 33/48

OTHER PUBLICATIONS

Kim et al., "Quantitative susceptibility mapping to evaluate the early stage of Alzheimer's disease," Neuroimage Clinical 16, Aug. 24, 2017, pp. 429-438.

*Primary Examiner* — Mahendra R Patel
(74) *Attorney, Agent, or Firm* — Foley & Lardner LLP (57) ABSTRACT

Provided is an image processor including a tissue-segmentation-processing-unit that performs tissue segmentation processing on at least one of a plurality of complex images generated based on a magnetic resonance signal generated from a subject to calculate a tissue-image related to a predetermined specific tissue, a magnetic-susceptibility-image-calculation-unit that calculates a magnetic-susceptibility-image showing magnetic susceptibility of a predetermined tissue included in the complex image from the complex image, an anatomical-standardization-processing-unit that calculates a standard-magnetic-susceptibility-image and a spatially-normalized tissue-image by performing spatially normalization processing on the magnetic-susceptibility-image and the tissue-image and calculates a volume modulated spatially-normalized tissue-image obtained by performing volume modulation on the spatially-normalized tissue-image, a magnetic-susceptibility-calculation-unit that calculates magnetic susceptibility of the specific tissue based on the spatially-normalized -magnetic-susceptibility-image and the spatially-normalized tissue-image, and a diagnostic-index-calculation-unit that calculates a diagnostic index for diagnosing a predetermined disease based on the magnetic (Continued)

susceptibility of the specific tissue and the volume modulated spatially-normalized tissue-image.

12 Claims, 7 Drawing Sheets (51) Int. Cl.
  *G01R 33/56* (2006.01)
  *G01R 33/44* (2006.01)
  *G06T 7/00* (2017.01)
  *G06T 7/174* (2017.01)
  *G06T 7/62* (2017.01)
  *A61B 5/00* (2006.01)
  *A61B 5/055* (2006.01)
  *G06T 11/00* (2006.01)

(52) U.S. Cl.
  CPC ........ *G01R 33/5608* (2013.01); *G06T 7/0012* (2013.01); *G06T 7/174* (2017.01); *G06T 7/62* (2017.01); *G06T 11/003* (2013.01); *G06T 2207/10088* (2013.01); *G06T 2207/20128* (2013.01); *G06T 2207/30016* (2013.01); *G06T 2207/30101* (2013.01)

(58) Field of Classification Search
  CPC ...... G01R 33/44; G01R 33/56; G01R 33/443; G01R 33/5608; G01R 33/56536; G06K 9/00; G06F 19/00; A61K 9/0019; H01F 7/20; A61M 37/00; H03M 1/745; G01N 33/50; A61B 5/00; A61B 5/055; A61B 5/0042; A61B 5/0555; A61B 6/5217

USPC .................... 382/131, 128; 324/309
  See application file for complete search history.

(56) References Cited

U.S. PATENT DOCUMENTS

| | | | | |
|---|---|---|---|---|
| 2010/0284595 | A1* | 11/2010 | Mori | G01R 33/56 382/131 |
| 2011/0044524 | A1* | 2/2011 | Wang | G01R 33/54 382/131 |
| 2011/0077503 | A1* | 3/2011 | Bonilha | A61B 5/055 600/411 |
| 2011/0098554 | A1* | 4/2011 | Mardor | A61K 9/0019 600/411 |
| 2013/0221961 | A1* | 8/2013 | Liu | G01R 33/56545 324/307 |
| 2013/0224117 | A1* | 8/2013 | Royall | G06F 19/00 424/9.2 |
| 2014/0039300 | A1* | 2/2014 | Gjesdal | G01R 33/5608 600/420 |
| 2014/0039320 | A1* | 2/2014 | Jespersen | A61B 8/488 600/454 |
| 2015/0338492 | A1* | 11/2015 | Sato | G01R 33/50 600/410 |
| 2015/0362575 | A1* | 12/2015 | Ourselin | G01R 33/5616 382/131 |
| 2015/0362578 | A1* | 12/2015 | Biber | G01R 33/3875 324/309 |
| 2016/0111192 | A1* | 4/2016 | Suzara | A61B 34/30 335/301 |
| 2017/0071522 | A1* | 3/2017 | Parsey | A61B 5/165 |

* cited by examiner

IMAGE PROCESSOR, IMAGE PROCESSING METHOD, PROGRAM FOR IMAGE PROCESSING, AND MAGNETIC RESONANCE IMAGING APPARATUS

BACKGROUND OF THE INVENTION

Field of the Invention

The present invention relates to an image processor, an image processing method, a program for image processing, and a magnetic resonance imaging apparatus, particularly to a technique for performing predetermined image processing on a reconstructed image showing tissue in a subject imaged by a magnetic resonance imaging apparatus.

Background Art

A magnetic resonance imaging apparatus (hereinafter, refer to as MRI apparatus) is an apparatus that applies a high frequency magnetic field and a gradient magnetic field to a subject placed in a static magnetic field, and measures a signal generated from the subject by nuclear magnetic resonance to acquire a medical image to be used for diagnosis.

The MRI apparatus is useful for image diagnosis of various diseases such as tumor and dementia. For example, in the diagnosis of Alzheimer's disease (AD), brain atrophy, which is one of pathological changes, can be visually evaluated using T1 weighted images excellent in the depiction of tissue structure. Also, by using diagnostic support software such as a voxel-based specific regional analysis system for Alzheimer's disease (VSRAD), the degree of atrophy can be quantitatively evaluated.

However, it is generally considered that it is difficult to make an accurate diagnosis merely by the morphological diagnosis by the T1 weighted image in the stage before the characteristic change in the brain volume occurs.

In recent years, a quantitatively susceptibility mapping (QSM) method has been proposed that estimates magnetic susceptibility distribution in a living body from a phase image by utilizing the fact that the phase image reflects the susceptibility difference between tissues. The QSM method is expected as a method for finding iron deposition occurring at an early stage of AD.

For example, Kim H G et al., Quantitative susceptibility mapping to evaluate the early stage of Alzheimer's disease, Neuroimage Clinical 2017 discloses a method of comparing the magnetic susceptibility in the brains of AD patients and healthy people calculated by the QSM method and diagnosing utilizing the fact that the magnetic susceptibility of the basal ganglia and cortex in the AD patients is larger than that of healthy people. Moreover, Kim H G et al., Quantitative susceptibility mapping to evaluate the early stage of Alzheimer's disease, Neuroimage Clinical 2017 discloses that a T1-weighted image is also imaged separately from the QSM image and used for removal of cerebrospinal fluid (CSF) not used for magnetic susceptibility evaluation and for spatially normalization to evaluate different subjects at the same coordinates (standard brain coordinates). Specifically, according to the method disclosed in Kim H G et al., Quantitative susceptibility mapping to evaluate the early stage of Alzheimer's disease, Neuroimage Clinical 2017, tissue segmentation processing is performed on a T1 weighted image to calculate gray matter images and white matter images showing the probabilities of existence in gray matter and white matter in voxels. Next, spatially normalization is performed on the gray matter image, white matter image, and magnetic susceptibility image, respectively, and magnetic susceptibility extraction and volume evaluation of a gray matter/white matter region are performed.

SUMMARY OF THE INVENTION

However, according to the method disclosed in the above-mentioned Kim H G et al., Quantitative susceptibility mapping to evaluate the early stage of Alzheimer's disease, Neuroimage Clinical 2017, since the T1 weighted image and the magnetic susceptibility image are separately imaged, when performing the magnetic susceptibility extraction and volume evaluation for each region, it is necessary to perform image registration processing of both, resulting in an registration error and an increase in calculation time. Moreover, since the gray matter image and the white matter image are simultaneously multiplied with the magnetic susceptibility image, information on magnetic susceptibility of the gray matter region and the white matter region is mixed. In addition, since the magnetic susceptibility extraction and brain volume evaluation are performed using the same gray matter image, there are cases where the volume information is mixed in the magnetic susceptibility or brain volume cannot be evaluated appropriately.

The present invention has been made in view of the above circumstances, and it is an object of the present invention to provide a highly accurate diagnostic index by extracting volume information and magnetic susceptibility information on gray matter/white matter with high accuracy.

In order to solve the above-described problems, the present invention provides the following means.

According to an aspect of the present invention, there is provided an image processor including: a tissue segmentation processing unit that performs tissue segmentation processing on at least one of a plurality of complex images generated based on a magnetic resonance signal generated from a subject to calculate a tissue image related to a predetermined specific tissue; a magnetic susceptibility image calculation unit that calculates a magnetic susceptibility image showing magnetic susceptibility of a predetermined tissue included in the complex image from the complex image; an spatially normalization processing unit that calculates a spatially-normalized magnetic susceptibility image and a spatially-normalized tissue image by performing spatially normalization processing on the magnetic susceptibility image and the tissue image and calculates a volume modulated spatially-normalized tissue image obtained by performing volume modulation on the spatially-normalized tissue image; a magnetic susceptibility calculation unit that calculates magnetic susceptibility of the specific tissue based on the spatially-normalized magnetic susceptibility image and the spatially-normalized tissue image; and a diagnostic index calculation unit that calculates a diagnostic index for diagnosing a predetermined disease based on the magnetic susceptibility of the specific tissue and the volume modulated spatially-normalized tissue image.

According to another aspect of the present invention, there is provided a magnetic resonance imaging apparatus including the above-described image processor.

According to the present invention, a highly accurate diagnostic index can be provided by extracting volume information and magnetic susceptibility information on gray matter/white matter with high accuracy.

DETAILED DESCRIPTION OF THE INVENTION

An image processor according to an embodiment of the present invention includes a tissue segmentation processing unit that performs tissue segmentation processing on at least one of a plurality of complex images generated based on a magnetic resonance signal generated from a subject to calculate a tissue image related to a predetermined specific tissue, a magnetic susceptibility image calculation unit that calculates a magnetic susceptibility image showing magnetic susceptibility of a predetermined tissue included in the complex image from the complex image, an spatially normalization processing unit that calculates a spatially-normalized magnetic susceptibility image and a spatially-normalized tissue image by performing spatially normalization processing on the magnetic susceptibility image and the tissue image and calculates a volume modulated spatially-normalized tissue image obtained by performing volume modulation on the spatially-normalized tissue image, a magnetic susceptibility calculation unit that calculates magnetic susceptibility of the specific tissue based on the spatially-normalized magnetic susceptibility image and the spatially-normalized tissue image, and a diagnostic index calculation unit that calculates a diagnostic index for diagnosing a predetermined disease based on the magnetic susceptibility of the specific tissue and the volume modulated spatially-normalized tissue image.

Hereinafter, embodiments of the present invention will be described in detail with reference to the drawings.

In the present embodiment, as an example, an example in which the above-described image processor is applied to a horizontal magnetic field type MRI apparatus will be described.

Figure 1:
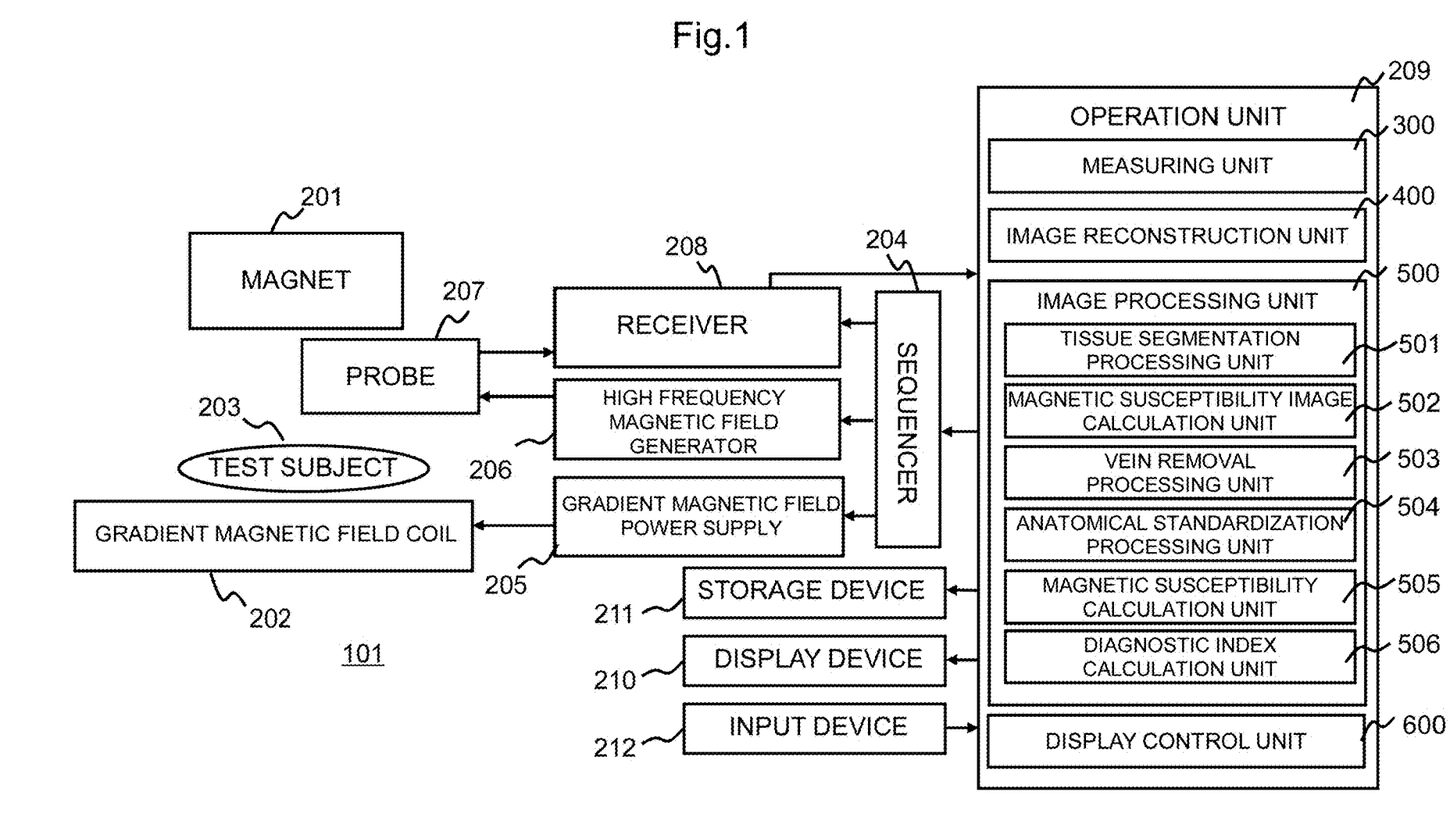
FIG. 1 is a block diagram showing a schematic configuration of an MRI apparatus to which an image processor according to an embodiment of the present invention is applied.

As shown in FIG. 1, an MRI apparatus 101 includes a magnet 201 that generates a static magnetic field in a direction parallel to a subject, a gradient magnetic field coil 202 that generates a gradient magnetic field, a sequencer 204, a gradient magnetic field power supply 205, a high frequency magnetic field generator 206, a probe 207 that irradiates a high frequency magnetic field and detects a nuclear magnetic resonance signal (echo), a receiver 208, an operation unit 209, a display device 210, and a storage device 211.

In the present embodiment, a coordinate system in which a static magnetic field direction of the MRI apparatus 101 is the z direction and the direction parallel to a placement surface of the subject in a bed is the x direction and the other direction is the y direction, out of the two directions perpendicular to the z direction.

A subject 203 such as a living body is placed on a bed (table) and the like, and placed in a static magnetic field space generated by the magnet 201. In the present embodiment, the following description will be made under an assumption that a head of a living body is a subject to be imaged and diagnosis is performed on brain diseases such as dementia and Alzheimer's disease using an imaged image.

The sequencer 204 sends a command to the gradient magnetic field power supply 205 and the high frequency magnetic field generator 206 according to an instruction from the operation unit 209 to be described later to generate a gradient magnetic field and a high frequency magnetic field, respectively. The generated high frequency magnetic field is applied to the subject 203 through the probe 207. An echo generated from the subject 203 is received by the probe 207 and detected by the receiver 208.

The receiver 208 performs detection according to a nuclear magnetic resonance frequency (detection reference frequency f0) serving as a reference of detection. The nuclear magnetic resonance frequency serving as a reference of detection is set by the sequencer 204. The receiver 208 outputs the detected signal to the operation unit 209. Herein, as necessary, a signal detected in the storage device 211, measurement conditions, image information after signal processing, and the like may be stored.

The sequencer 204 controls each unit to operate at each timing and strength previously programmed. Among the programs, in particular, the high frequency magnetic field, the gradient magnetic field, the timing and strength of signal reception are described as a pulse sequence.

In the present embodiment, in order to calculate the magnetic susceptibility based on the change in the magnetic field obtained from the phase image, a pulse sequence which acquires at least one echo with a shifted phase is used. In the following description, in particular, a pulse sequence of Gradient Echo (GrE) system capable of obtaining a signal depending on the non-uniformity in a spatial distribution of the magnetic field strength is used. The pulse sequence of the GrE system includes, for example, an RF-spoiled-Steady-state Acquisition with Rewound Gradient-Echo (RSSG) sequence.

The operation unit 209 functions as a central processing unit (CPU) and controls the entire MRI apparatus. That is, the sequencer 204 is controlled so as to measure the echo according to imaging conditions input through an input device 212 or preset imaging conditions (measurement parameters and pulse sequence). Furthermore, the operation unit 209 performs predetermined arithmetic processing including image reconstruction and calculation of magnetic susceptibility image on the echo obtained by the measurement, and causes the display device 210 to display the processed image. In addition, as necessary, ROI is set on the processed image and the statistical value of a pixel in the ROI is calculated.

Figure 2:
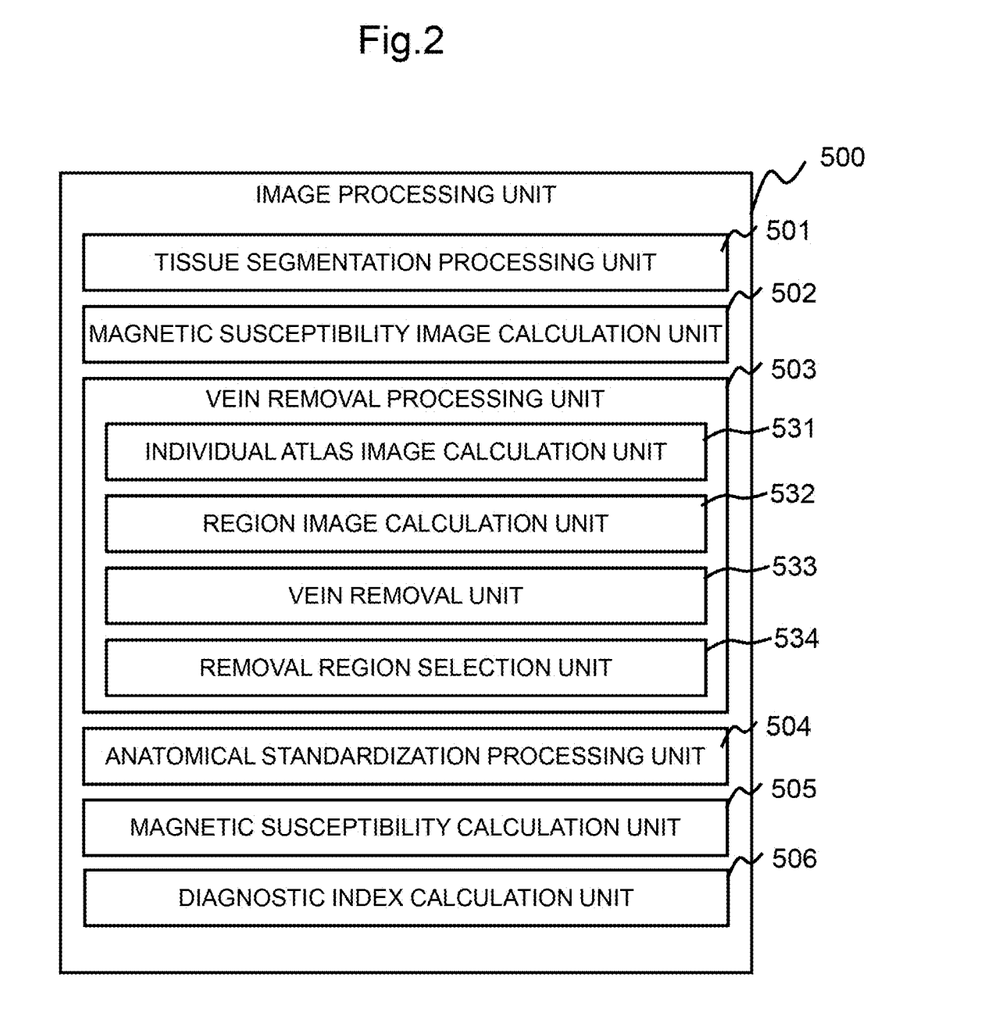
FIG. 2 is a block diagram showing a schematic configuration of the image processor according to the embodiment of the present invention.

Therefore, as shown in FIGS. 1 and 2, the operation unit 209 realizes functions of a measuring unit 300, an image reconstruction unit 400, an image processing unit 500, and a display control unit 600. These functions of the respective units realized by the operation unit 209 can be realized as software by the operation unit 209 reading and executing the program stored in the storage device 211 and the like in advance. Moreover, part or all of the operations executed by each unit included in the operation unit 209 can be realized by an application specific integrated circuit (ASIC) or a field-programmable gate array (FPGA).

When various measurement parameters are set, upon receipt of an instruction to start imaging, the measuring unit 300 instructs the sequencer 204 according to a predetermined pulse sequence to acquire an echo signal and disposes the echo signal in a k space.

Figure 3:
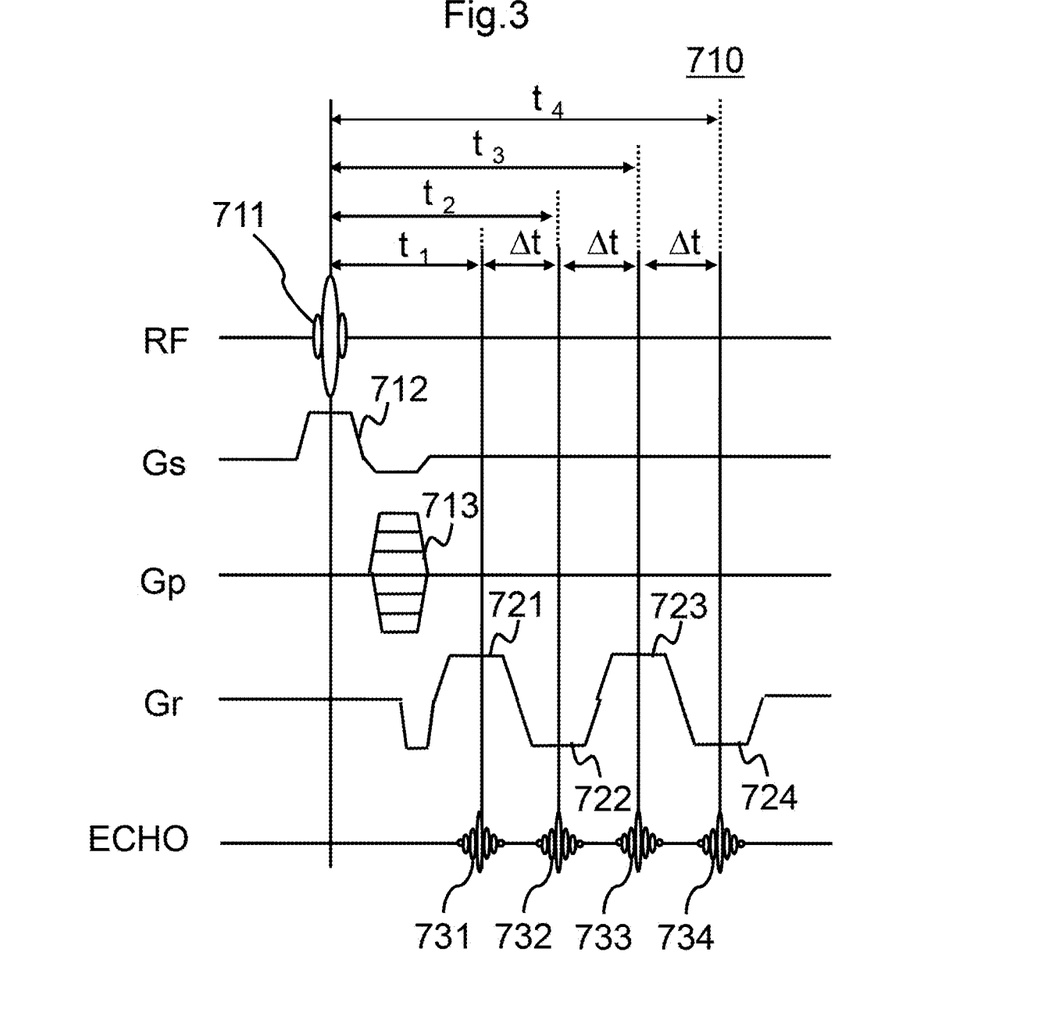
FIG. 3 is a reference chart showing a time chart of a measurement sequence by the MRI apparatus according to the embodiment of the present invention.

FIG. 3 shows an example of a time chart of the measurement sequence instructed to the sequencer 204 by the measuring unit 300. A measurement sequence 710 shown in FIG. 3 is a gradient echo (GrE) type pulse sequence. In the measurement sequence 710, RF represents the application timing of an RF pulse, Gs represents the application timing of a slice selection gradient magnetic field, Gp represents the application timing of a phase encoding gradient magnetic field, and Gr represents the application timing of a readout gradient magnetic field, respectively. In addition, $t_1$ represents a first echo time, and $\Delta t$ represents the subsequent echo time interval (echo interval). Echo indicates the acquisition timing of the echo signal.

In the measurement sequence 710, the echo signal is measured within one repetition time TR by the following procedure. The measuring unit 300 acquires two or more echoes with different echo times in order to make a T1 weighted imaging method realizable with a short echo time (for example, 4 milliseconds, called shortest TE) compatible with a QSM method realizable with a long echo time (for example, 30 milliseconds, called longest TE) in one sequence.

As shown in FIG. 3, in the present embodiment, as an example, the echo signal is acquired with four different echo times in one sequence. Hereinafter, the echo signal acquired at an echo time $t_1$ is referred to as a first echo signal and a complex image obtained from the first echo signal is referred to as a first original image, and hereinafter, similarly, referred to as a second echo signal, a third echo signal, a fourth echo signal, a second original image, a third original image, and a fourth original image. The number of different echo times, that is, the number of original images is not limited to four, but is optional. Further, non-Cartesian imaging may be used such as a radial scan for acquiring data in a rotation pattern in a k space.

The image reconstruction unit 400 performs image reconstruction processing for reconstructing an image from each echo signal with respect to a plurality of echo times measured according to an instruction from the measuring unit 300. In the present embodiment, the image reconstruction unit 400 acquires a complex image in which each pixel value is a complex number by the image reconstruction processing.

The image processing unit 500 performs various image processing described later such as calculation of gray matter image and magnetic susceptibility image based on the obtained complex image. Details of the image processing unit 500 and the flow of image processing in the image processing unit 500 will be described later.

The display control unit 600 causes the display device 210 to display various images including gray matter images, magnetic susceptibility images, and the like obtained by the image processing unit 500 as grayscale images.

Hereinafter, details of the image processing unit 500 will be described in more detail.

Figure 4:
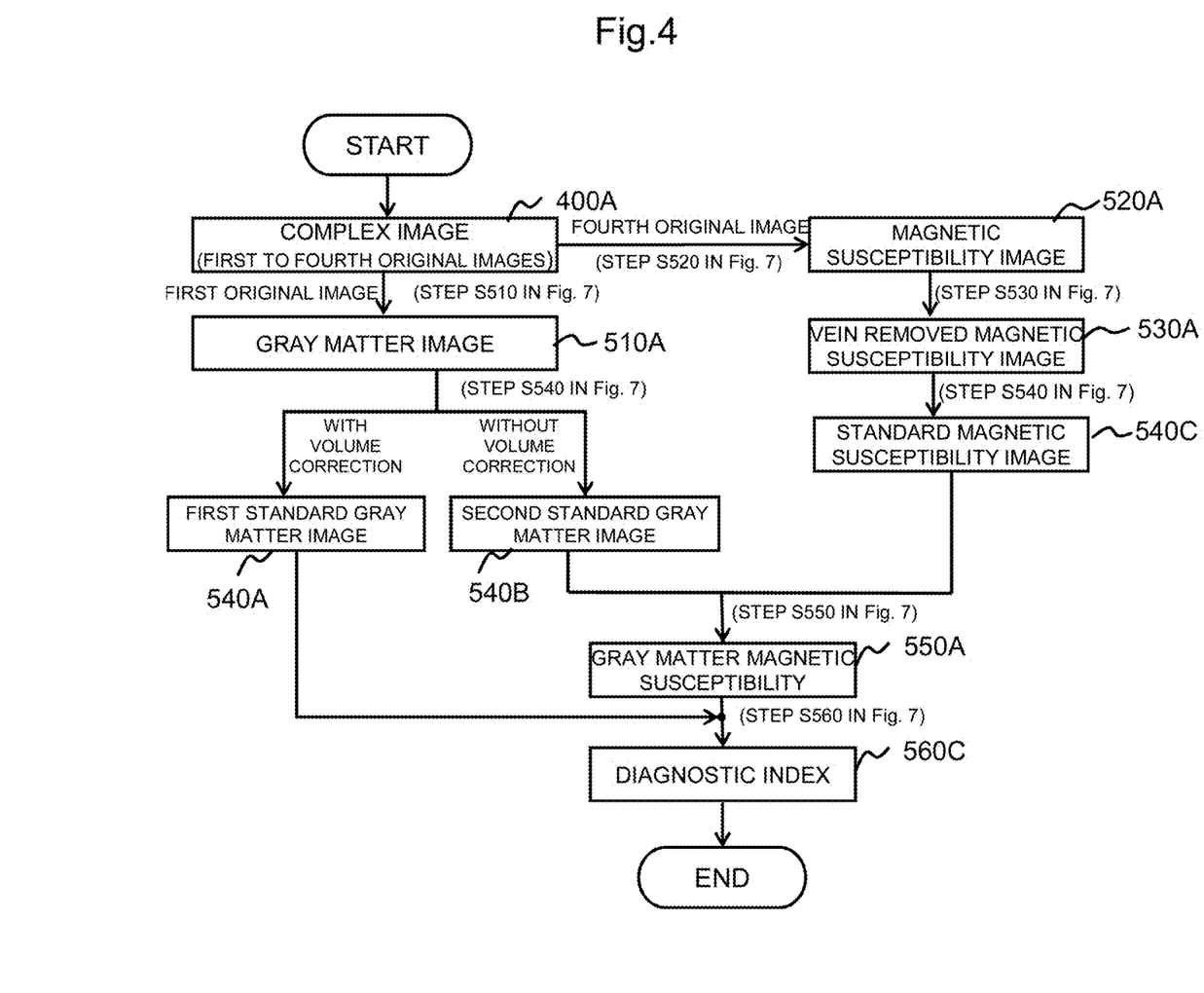
FIG. 4 is a reference diagram showing images and the like generated along a process flow in an image processing unit of the MRI apparatus according to the embodiment of the present invention.

As shown in FIGS. 1 and 2, in order to execute the above-described processing, the image processing unit 500 includes a tissue segmentation processing unit 501, a magnetic susceptibility image calculation unit 502, a vein removal processing unit 503, an spatially normalization processing unit 504, a magnetic susceptibility calculation unit 505, and a diagnostic index calculation unit 506 for calculating a diagnostic index. FIG. 4 shows a reference diagram showing images and the like calculated along a process flow in the image processing unit 500.

The tissue segmentation processing unit 501 performs tissue segmentation processing and segments a complex image 400A acquired by the image reconstruction unit 400 into tissue images such as a gray matter region, a white matter region, and a cerebrospinal fluid region. The pixel value in each tissue image is a value in the range of 0 to 1, and represents the probability of existence of each tissue (gray matter, white matter, cerebrospinal fluid). For the tissue segmentation processing, a known method used in a previous study (Good et al., A voxel-based morphometric study of ageing in 465 normal adult human brains, Neuroimage) is used.

In the present embodiment, the description will be made under an assumption that the tissue segmentation processing is performed on the first original image among the plurality of complex images (first original image to fourth original image) obtained within one pulse sequence, and an example in which gray matter image 510A among the various images obtained by the tissue segmentation processing is used for subsequent processing will be described.

The magnetic susceptibility image calculation unit 502 calculates a magnetic susceptibility image from the input image. For example, the calculation of the magnetic susceptibility image is carried out by a known method (for example, a method described in Sato et al., Quantitative Susceptibility Mapping Using the Multiple Dipole-Inversion Combination with k-space Segmentation Method, Magnetic Resonance in Medical Sciences). In the present embodiment, a magnetic susceptibility image 520A is calculated using the fourth original image (absolute value image and phase image) which is the final echo.

Specifically, the calculation of the magnetic susceptibility image is performed as follows. The magnetic susceptibility image calculation unit 502 first calculates a mask image which defines a brain region from the absolute value image of the fourth original image by threshold processing or the like. The mask image is a binary image in which the brain region is set to 1 and the other regions are set to 0. Next, unwrapping processing is performed on the phase image by a region growing method or the like.

Next, on the unwrapped phase image, background magnetic field removal processing for calculating a local magnetic field due to magnetic susceptibility difference between living tissues or the like is performed except for a global magnetic field change due to magnetic susceptibility difference and the like between inside and outside the body. In the present embodiment, for example, background magnetic field removal processing is performed using a known regularization enabled sophisticated harmonic artifact reduction for phase data (RESHARP) method.

Thereafter, the magnetic susceptibility is calculated based on a relational expression between the magnetic field change and the magnetic susceptibility distribution. In the present embodiment, for example, a method of repeating smoothing processing on the magnetic susceptibility distribution calculated from the magnetic field distribution under a constraint condition based on the relational expression between the magnetic field and the magnetic susceptibility (disclosed in Japanese Patent No. 6289664 by the present inventors) is used. Alternatively, it can be obtained by a method of calculating the magnetic susceptibility by applying different processing for each region of k space called a multiple dipole-inversion combination with k-space segmentation (MUDICK) method. Alternatively, a method using a constraint term called regularization or the like may be used.

In the present embodiment, the magnetic susceptibility image is calculated using the fourth original image, but the magnetic susceptibility image maybe calculated using any one of the first to fourth original images. Further, the magnetic susceptibility image may be calculated using all the images. A known method (for example, Wu et al., Fast and tissue-optimized mapping of magnetic susceptibility and T2* with multi-echo and multi-shot spirals, NeuroImage) is used for calculating the magnetic susceptibility image from a plurality of echo times. When all the images are used, calculation time generally increases compared to one image, but magnetic susceptibility images with less noise can be obtained.

As shown in FIG. 2, the vein removal processing unit 503 removes a vein on the magnetic susceptibility image, and includes an individual atlas image calculation unit 531, a region image calculation unit 532, a vein removal unit 533, and a removal region selection unit 534.

The individual atlas image calculation unit 531 calculates an individual atlas image by inversely transforming a general atlas image defined on a standard brain. That is, an individual atlas image is calculated by performing transformation processing opposite to the transformation processing of applying the standard brain coordinate system to the subject's brain image on which the spatially normalization is performed.

The same parameters used in the spatially normalization processing can be used as parameters in this inverse transformation processing. When performing inverse transformation, in the present embodiment, interpolation processing is performed by nearest neighbor interpolation. By using the calculated individual atlas image, it is possible to identify the location of an anatomically defined region on the same coordinate as the magnetic susceptibility image. For example, an automated anatomical labeling (AAL) atlas is used as the atlas image.

The region image calculation unit 532 calculates a basal ganglia mask image only the basal ganglia region is set to 1 and the rest is set to 0 and calculates an outer basal ganglia mask image in which the brain region other than the basal ganglia is set to 1, and the rest is set to 0 from the individual atlas image obtained by the individual atlas image calculation unit 531.

In the basal ganglia mask image in this embodiment, the pixel value of the basal ganglia region defined as the putamen, the caudate nucleus, the globus pallidus, and the thalamus on the individual atlas image is set to 1, and the other region is set to 0. The outer basal ganglia mask image is an image obtained by subtracting the basal ganglia mask image from the mask image calculated by the magnetic susceptibility image calculation unit 502 for each pixel. By using the basal ganglia mask or the outer basal ganglia mask image generated in this manner, it is possible to extract an image obtained by separating a region related to a predetermined structure in the magnetic susceptibility image use the extracted image for subsequent processing.

The vein removal unit 533 acquires a vein removed magnetic susceptibility image 530A from which a vein on the magnetic susceptibility image is removed by performing the following processing on the magnetic susceptibility image. That is, a vein removal unit first performs line emphasis processing on the magnetic susceptibility image for each slice using a Sobel filter or the like, and creates an image in which the vein region emphasized. Since this processing emphasizes the line segment region, the boundary between the white matter and gray matter is also emphasized in addition to veins.

Next, a vein mask image is obtained by performing the threshold processing on the magnetic susceptibility image in which the line segment region is emphasized to extract only veins. In the vein mask image, the vein region is set to 1 and the other region is set to 0. The threshold value in this embodiment is set to 0.03 ppm, and a region having a threshold value equal to or larger than the threshold value is set to 1, and a region having a threshold value below the threshold value is set to 0.

Finally, in the magnetic susceptibility image, a vein removed magnetic susceptibility image 530A is obtained by replacing the magnetic susceptibility of the vein region discriminated by the vein mask image with the average value of the peripheral pixels. In this processing, a kernel is set for each pixel in the vein region, and the corresponding pixel value is set as the average pixel value of a region other than the vein region in the kernel. The kernel size in this embodiment is 7×7 pixels.

The removal region selection unit 534 calculates the selective vein removed magnetic susceptibility image based on the vein removed magnetic susceptibility image as necessary. The selective vein removed magnetic susceptibility image is calculated by adding the image obtained by multiplying the magnetic susceptibility image by the basal ganglia mask image and the image obtained by multiplying the vein removed magnetic susceptibility image by the outer basal ganglia mask image.

Figure 5:
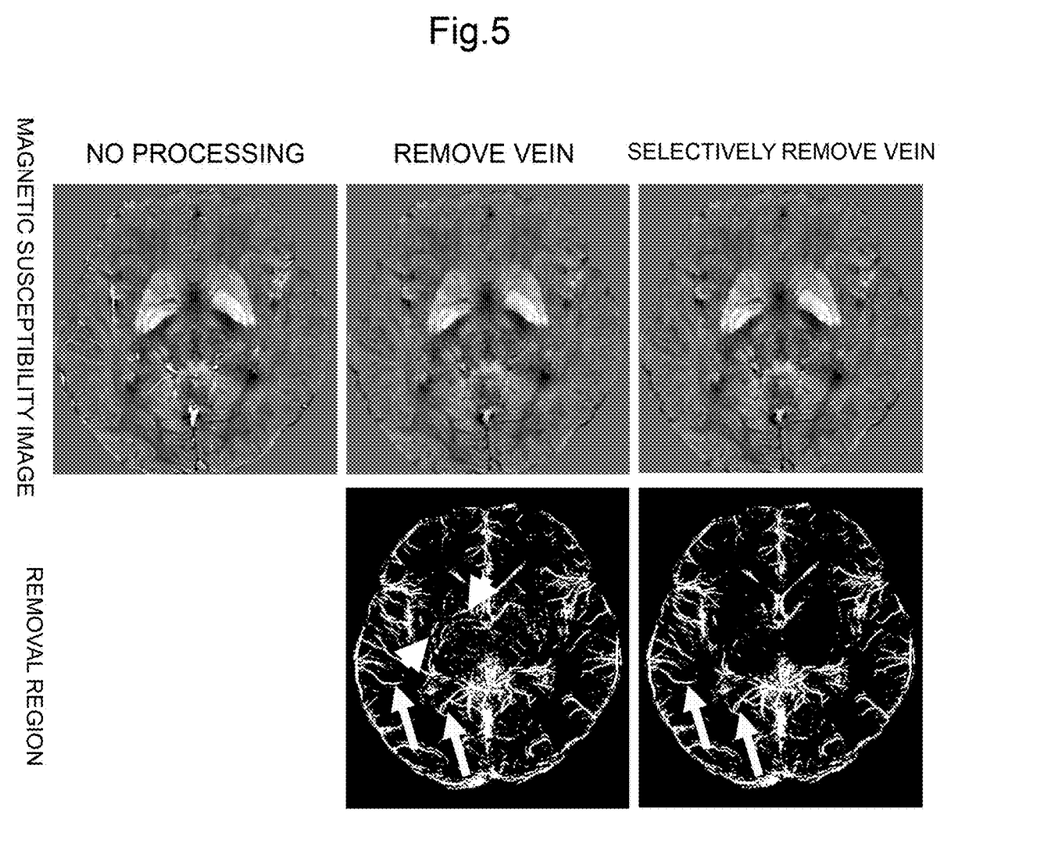
FIG. 5 is a reference diagram showing an example of an image generated by processing in the image processing unit of the MRI apparatus according to the embodiment of the present invention.

FIG. 5 shows the magnetic susceptibility image, the vein removed magnetic susceptibility image generated by the vein removal processing unit 503, and the selective vein removed magnetic susceptibility image. In addition, removed regions in each image are shown. As shown in FIG. 5, the vein removed magnetic susceptibility image shows that the structure of the basal ganglia is also removed in addition to the cortical vein. On the other hand, in the selective vein removed magnetic susceptibility image, it is found that veins are removed while leaving the structure of the basal ganglia. As described above, by performing selective vein removal processing, the magnetic susceptibility of the cortex and the basal ganglia can be extracted with high accuracy.

The processing by the individual atlas image calculation unit 531, the region image calculation unit 532, and the removal region selection unit 534 may be omitted. In that case, although the structure of the basal ganglia region is removed, the calculation time can be shortened because the operation of individual brain transformation can be omitted.

Moreover, processing may be performed with different threshold values for each region showing a predetermined structure. For example, with respect to the basal ganglia region, a threshold value is set to 0 ppm, a region having a threshold value equal to or lower the threshold value is set to 1 and a region having a threshold value above the threshold value is set to 0 so that a calcification mask for removing the calcified region deposited on the globus pallidus or putamen may be calculated.

It is possible to obtain a calcification removed magnetic susceptibility image by replacing the magnetic susceptibility of the calcified region with the average value of the peripheral pixels using the calculated calcification mask. A magnetic susceptibility image from which the calcified region of the basal ganglia and the cortical vein are removed can be calculated by adding an image obtained by multiplying the calcification removed magnetic susceptibility image by the basal ganglia mask image and an image obtained by multiplying the vein removed magnetic susceptibility image by the outer basal ganglia mask image, and thereby the iron deposits at both sites can be evaluated with high accuracy.

Similarly, in order to further separate the region related to the structure outside the basal ganglia from the magnetic susceptibility image, the parameters for filtering processing and the above-described kernel size may be changed for each region. For example, since the inner cerebral vein is generally larger in diameter than the other veins, the kernel size may be increased only in the region where the inner cerebral vein exists. Moreover, the vein removal processing may not be necessarily performed.

The spatially normalization processing unit 504 performs spatially normalization processing on the input image to calculate a first standard gray matter image (volume modulated spatially-normalized tissue image) 540A, a second standard gray matter image (spatially-normalized tissue image) 540B, and a spatially-normalized magnetic susceptibility image 540C. The first standard gray matter image is used for volume calculation and the second standard gray matter image is used for weighting processing of magnetic susceptibility image.

Here, the spatially normalization processing means converting the brain image of each subject to a standard brain coordinate system and matching it with the standard brain image, so that the position of each structure of the brain can be grasped coordinates. For example, a diffeomorphic anatomical registration through exponentiated lie algebra (DARTEL) method is used for the spatially normalization according to the present embodiment.

In the present embodiment, the following image is calculated by the spatially normalization processing unit 504 (see FIG. 4). That is, the first standard gray matter image as an image obtained by performing volume modulation with the spatially normalization processing on the gray matter image obtained based on the first original image by the tissue segmentation processing unit 501. Moreover, the standard gray matter image is an image obtained by performing the spatially normalization processing without performing volume modulation on the gray matter image obtained based on the first original image by the tissue segmentation processing unit 501.

Furthermore, the spatially-normalized magnetic susceptibility image is an image obtained by performing spatially normalization processing without performing volume modulation on the selective vein removed magnetic susceptibility image obtained in the vein removal processing unit 503. The magnetic susceptibility image calculation unit 502 may calculate the spatially-normalized magnetic susceptibility image based on the magnetic susceptibility image obtained based on the fourth original image.

Generally, volume modulation is a process called modulation, which is processing of restoring volume information lost by the spatially normalization processing. Therefore, by performing volume modulation, the pixel value of the standard gray matter image reflects the brain volume. On the other hand, when volume modulation is not performed, the pixel value of the standard gray matter image reflects the existence probability.

In the present embodiment, accurate information on the gray matter volume can be reflected in the diagnostic index by using the first standard gray matter image subjected to the volume modulation in the diagnostic index calculating unit. Moreover, it is possible to extract the gray matter region by using the second standard gray matter image not subjected to volume modulation in the magnetic susceptibility calculation unit while preserving information on the volume susceptibility without mixing brain volume information.

In the previous study (Langkammer et al., Quantitative susceptibility mapping (QSM) as a means to measure brain iron? A post mortem validation study, Neuroimage, etc.), it is shown that the magnetic susceptibility of gray matter varies mainly due to the concentration of iron, while the susceptibility of white matter changes not only by iron but also by several influences such as myelin. It is possible to accurately evaluate the rise of iron due to Alzheimer's disease by extracting the magnetic susceptibility of only the gray matter with high accuracy using the image processor according to the present embodiment as described above.

The second standard gray matter image may be used as a weight. For example, a weighted average of the pixel value of the standard susceptibility image with the pixel value of the second standard gray matter image as a weight within an optional region (such as orbital frontal cortex) defined by the atlas image may be calculated to be the gray matter magnetic susceptibility of the region. Specifically, the weighted average value x is calculated by the following Expression (1).

$$x = \Sigma_i(w_i \cdot x_i)/\Sigma_i w_i \quad (1)$$

Here, $w_i$ represents the pixel value of the second standard gray matter image at the pixel i, $x_i$ represents the pixel value of the standard susceptibility image, and $\Sigma_i$ represents an operator for calculating the sum of the pixel values within a specified region. By this calculation, it is possible to calculate the average magnetic susceptibility of only the gray matter in the specified region.

In the spatially normalization processing unit 504, the spatially normalization processing may be performed on the white matter image instead of the gray matter image to calculate a first white matter image (with volume modulation) and a second white matter image (without volume modulation). The first white matter image can be used for volume evaluation of white matter and the second white matter image can be used for extraction of white magnetic susceptibility.

The magnetic susceptibility calculation unit 505 calculates gray matter magnetic susceptibility 550A based on the standard gray matter image and the spatially-normalized magnetic susceptibility image. Specifically, the magnetic susceptibility calculation unit 505 calculates the gray matter magnetic susceptibility by multiplying the standard gray matter image and the spatially-normalized magnetic susceptibility image for each voxel. It is possible to evaluate cortical iron deposition without getting mixed with magnetic susceptibility of white matter and magnetic susceptibility of cerebrospinal fluid by calculating the gray matter magnetic susceptibility.

The magnetic susceptibility calculation unit 505 may calculate the white matter magnetic susceptibility. For example, the white matter magnetic susceptibility can be calculated by multiplying a second standard white matter image and the spatially-normalized magnetic susceptibility image for each voxel, and the white matter demyelination can be evaluated by calculating the white matter magnetic susceptibility without getting mixed with magnetic susceptibility of gray matter and magnetic susceptibility of cerebrospinal fluid.

The sum of gray matter magnetic susceptibility and white matter magnetic susceptibility may be used. In this case, there is a problem that magnetic susceptibility information on gray matter and white matter are mixed, but depending on the region, there is a possibility that the sensitivity may be improved by using the two magnetic susceptibility rises of iron deposition and demyelination.

The difference between gray matter magnetic susceptibility and white matter magnetic susceptibility may be acquired to calculate the medullary contrast for each region. In this case, it is possible to evaluate the medullary contrast associated with iron deposition in gray matter and demyelination in white matter. For example, the myelinated contrast increases in the region where the magnetic susceptibility of gray matter is improved by iron deposition, and the myelinated contrast decreases in the region where the magnetic susceptibility of white matter is improved by demyelination.

The diagnostic index calculation unit 506 calculates a diagnostic index d (560C) contributing to diagnosis regarding brain diseases such as dementia and Alzheimer's disease based on the gray matter magnetic susceptibility calculated by the magnetic susceptibility calculation unit 505 and the first gray matter image calculated by the spatially normalization processing unit 504.

For example, the average gray matter volume $m_h$ in the hippocampus region is calculated from the first gray matter image, the average susceptibility $x_p$ of the putamen region is calculated from the gray matter magnetic susceptibility image, and the sum thereof is taken as the diagnostic index d (Expression (2)).

$$d = -m_h + x_p \qquad (2)$$

The hippocampus region and putamen region are defined using, for example, an AAL atlas. Expression (2) above indicates that as $m_h$ is smaller and $x_p$ is larger, d becomes larger. This diagnostic index d has better diagnostic ability compared to the diagnostic index that depends only on the average gray matter volume because the information on iron deposition is added to this diagnostic index d.

Any method using the brain volume information and magnetic susceptibility information in combination can be used to calculate diagnostic index. For example, the deviation amount (z score) may be calculated from the healthy database for each of the average gray matter volumes in the hippocampus region and the average magnetic susceptibility of the putamen region, and the diagnostic index may be calculated from the sum thereof (Expression (3)).

$$d = -z^m{}_h + z^x{}_p \qquad (3)$$

For example, the z score in the gray matter volume of the hippocampus is calculated from the mean value $\mu^m{}_h$ and the standard deviation $\sigma^m{}_h$ of all subjects in the healthy database by the following equation (Expression (4)).

$$z^m{}_h = (m_h - \mu^m{}_h)/\sigma^m{}_h \qquad (4)$$

Alternatively, the diagnostic index may be calculated from the gray matter volume and gray magnetic susceptibility of a plurality of regions. For example, a diagnostic index is calculated by the following Equation (5) using z scores ($z^m{}_\alpha$, $z^x{}_\alpha$, $\alpha$ represents an arbitrary region) of the plurality of regions.

$$d = -\Sigma_\alpha \beta^m{}_\alpha \cdot z^m{}_\alpha + \Sigma_\alpha \beta^x{}_\alpha \cdot z^x{}_\alpha \qquad (5)$$

Here, $\beta^m{}_\alpha$ and $\beta^x{}_\alpha$ are any coefficients. Diagnostic accuracy improves by using information on the plurality of regions.

Any nonlinear function may be used to calculate the diagnostic index. For example, a diagnostic index may be calculated assuming a model in which the magnetic susceptibility increases in the early stage of dementia and the atrophy occurs later.

Figure 6:
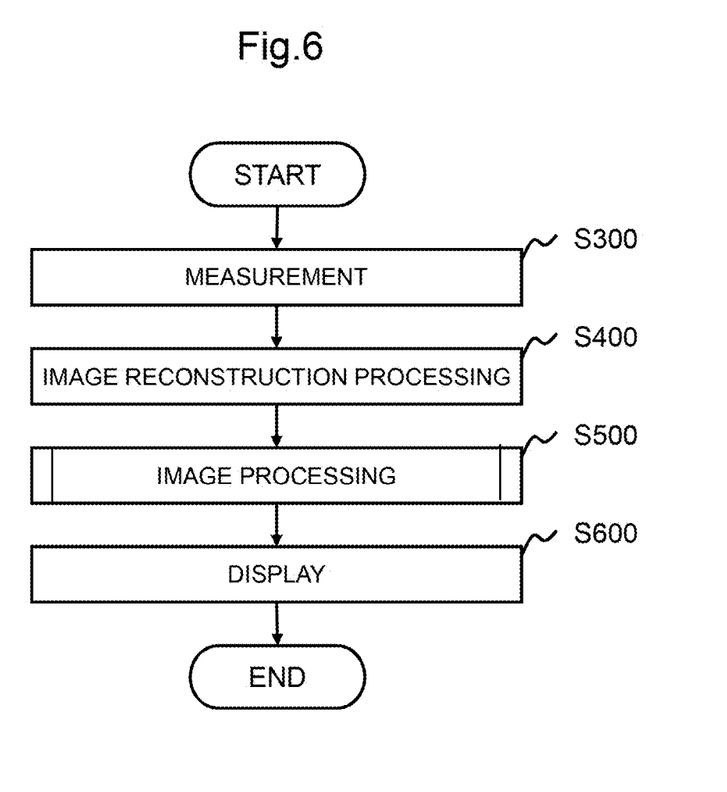
FIG. 6 is a flowchart showing an imaging process flow by the MRI apparatus in the MRI apparatus according to the embodiment of the present invention.

The imaging processing in the MRI apparatus configured in this way will be described below with reference to the flowchart of FIG. 6

In step S300, when various measurement parameters are set and receive an instruction to start imaging, the measuring unit 300 measures, that is, instructs the sequencer 204 according to a predetermined pulse sequence to obtain an echo signal. In accordance with the instruction, the sequencer 204 sends instructions to the gradient magnetic field power supply 205 and the high frequency magnetic field generator 206 as described above to generate a gradient magnetic field and a high frequency magnetic field, respectively. In the measuring unit 300, an echo received by the probe 207 and detected by the receiver 208 is received as a complex signal.

As described above, in the present embodiment, the GrE system pulse sequence exemplified in FIG. 3 is used. At this time, the repetition time is set to a time longer than the longest TE, 40 ms here. Further, a flip angle in the present embodiment is set to a value at which the contrast to noise ratio of the gray matter and the white matter in the T1 weighted image is maximized. In this case, it is assumed to be 45 degrees. These parameters are optional.

In FIG. 3, an RF pulse 711 is irradiated to excite the hydrogen nuclear spin of the subject 203. At this time, in order to select a specific slice of the subject 203, a slice selection gradient magnetic field (Gs) 712 is applied simultaneously with the RF pulse 711. Subsequently, a phase encoding gradient magnetic field (Gp) 713 for phase encoding the echo signal is applied.

Thereafter, a readout gradient magnetic field (Gr) 721 is applied after a time t1 from the first irradiation with the RF pulse 711 to measure the echo signal (first echo signal) 731. Further, at time t2 after time Δt is passed from the measurement of the first echo signal 731, the echo signal (second echo signal) 732 is measured by applying a read gradient magnetic field (Gr) 722 whose polarity has been inverted. Similarly, an echo signal (third echo signal) 733 is measured by applying a readout gradient magnetic field (Gr) 723 whose polarity has been inverted at time t3 after time Δt is passed from the measurement of the second echo signal 732. Further, an echo signal (fourth echo signal) 734 is measured by applying the readout gradient magnetic field (Gr) 724 whose polarity has been inverted at time t4 after time Δt is passed from the measurement of the third echo signal 733.

The measuring unit 300 repeats the irradiation of the RF pulse 711 to the predetermined imaging region of the subject 203 and the measurement of the echo signals 731, 732, 733, and 734 from the same region a predetermined number of times while changing the strength of the phase encoding gradient magnetic field 713 in the measurement sequence 710. The number of repetition is, for example, 128 times, 256 times, and the like.

Accordingly, the number of echo signals necessary for image reconstruction of the imaging region is repeatedly acquired. One original image (first original image) is formed by the first echo signal 731 for the number of times of repetition, and the second original image, the third original image, and the fourth original image are formed by the second echo signal 732, the third echo signal 733, and the fourth echo signal 734 for the number of repetitions, respectively. These are stored in the storage device or the like as an original image for calculation for calculating gray matter image and magnetic susceptibility image.

Upon completion of the measurement, in step S400, the image reconstruction unit 400 performs image reconstruction processing for reconstructing an image from the echo signals of the measured echo times t1, t2, t3, and t4. Here, each echo signal is placed in the k space and subjected to Fourier transformation. Accordingly, the first original image, the second original image, the third original image, and the fourth original image corresponding to the respective echo times t1, t2, t3, and t4 are calculated. Each calculated original image is a complex image in which each pixel value is a complex number.

Thereafter, in step S500, various processing is performed on the obtained complex image by the image processing unit 500 up to the calculation of the diagnostic index (details will be described later).

In the next step S600, the display control unit 600 causes the display device 210 to display the diagnostic index calculated by the image processing unit 500 in step S500, and the gray matter image and the magnetic susceptibility image subjected to the spatially normalization. The magnetic susceptibility image may be displayed by integrating a plurality of spatially continuous image information using methods such as maximum value projection processing and minimum value projection processing.

A region where the deviation from the average value of a healthy person is large, that is, an abnormal region of magnetic susceptibility may be displayed by a color map or the like on the magnetic susceptibility image. In this case, first, the magnetic susceptibility images of a plurality of healthy people are acquired, the average value and the standard deviation of all the subjects in each pixel on the standard brain coordinate are calculated, and these values are stored in the storage device 211 beforehand. Next, in each pixel of the magnetic susceptibility image on the standard brain coordinate, the amount of deviation from the average value normalized by the standard deviation is calculated. Finally, regarding the region where the calculated amount of deviation is equal to or greater than a certain threshold value (for example 2), the shift amount is color-displayed on the magnetic susceptibility image displayed in monochrome.

Figure 7:
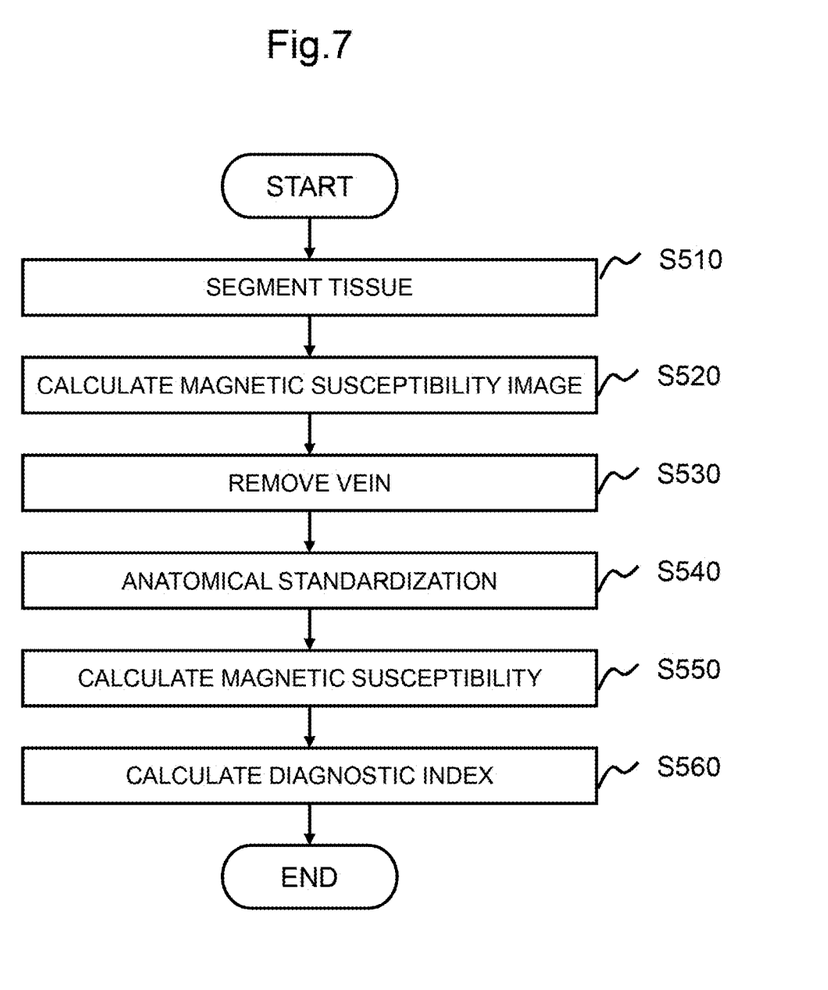
FIG. 7 is a flowchart showing the flow up to diagnostic index calculation by the image processing unit of the MRI apparatus according to the embodiment of the present invention.

Next, the image processing up to the calculation of the diagnostic index at step S500 in the flowchart of FIG. 6, which is executed by the image processing unit 500, will be described with reference to the flowchart of FIG. 7.

The tissue segmentation processing unit 501 segments each tissue image into gray matter regions, white matter regions, cerebrospinal fluid region, and the like by performing tissue segmentation processing on the first original image reconstructed by the image reconstruction unit 400 and stored in the storage device 211, and obtains, in particular here, the gray matter image (510A in FIG. 4) (step S510).

Following the processing of step S510 or in parallel with the processing of step S510, the magnetic susceptibility image calculation unit 502 generates magnetic susceptibility images (520A in FIG. 4) based on the fourth original image stored in the storage device 211 (Step S520). Next, in step S530, the vein removal processing unit 530 removes the vein on the magnetic susceptibility image calculated in step S520, and calculates the vein removed magnetic susceptibility image (530A in FIG. 4).

In the next step S540, the spatially normalization processing is performed on the gray matter image obtained in step S510 and the vein removed magnetic susceptibility image obtained in step S530 by the spatially normalization processing unit 504, the first standard gray matter image (540A in FIG. 4) and the second standard gray matter image (540B in FIG. 4) are calculated from the gray matter image, and the spatially-normalized magnetic susceptibility image (540C in FIG. 4) is calculated from the vein removed magnetic susceptibility image.

In the next step S550, the magnetic susceptibility calculation unit 505 calculates the gray matter magnetic susceptibility (550A in FIG. 4) by multiplying the second standard gray matter image and the spatially-normalized magnetic susceptibility image for each voxel. Finally, in step S560, the diagnostic index calculation unit 506 calculates a diagnostic index (560A in FIG. 4) based on the gray magnetic susceptibility and the first gray matter image.

As described above, according to the present embodiment, the gray matter magnetic susceptibility information is obtained using the gray matter image and the spatially-normalized magnetic susceptibility image obtained by the tissue segmentation processing, so that it is possible to obtain highly accurate gray matter magnetic susceptibility information in which volume information, magnetic susceptibility of white matter, magnetic susceptibility of a vein and the like are not mixed. In addition, since the diagnostic index is calculated by using the first standard gray matter image having the brain volume information together, a high-precision diagnostic index can be provided from the early stage in which iron deposition occurs in the cortex or the basal ganglia to the advanced stage of the atrophic pathology.

Since echo signals are acquired with a plurality of different echo times in one sequence, it is possible to calculate gray matter images and magnetic susceptibility images in one measurement. Accordingly, in the subsequent processing, it is unnecessary to perform the image registration of both images, so that an increase in calculation time accompanying the image registration processing and a reduction in accuracy due to an image registration error do not occur.

It is not always necessary to acquire the T1 weighted image and the magnetic susceptibility image by the same image imaging, but they may be obtained by separate imaging. Moreover, in the present embodiment, the magnetic susceptibility image has been described as an example, but another quantitative image may be used. For example, the T1 weighted image and the diffused image may be separately acquired and the above-described processing may be performed to calculate the diagnostic index from the brain volume information and the diffusion information on the specific tissue.

Although the target disease of the diagnostic index to be calculated has been described as dementia or a brain disease such as Alzheimer's disease, it is not limited thereto and can be applied to any diseases. For example, it can be applied to neurodegenerative diseases such as Parkinson's disease. In that case, a diagnostic index is calculated using different coefficients ($\beta^m_\alpha$ and $\beta^x_\alpha$) for each disease.

Although the tissue magnetic susceptibility is calculated for QSM images in this study, the same calculation may be performed on other quantitative images. For example, similar calculations may be performed on images (T1 image, T2 image) representing the distribution of relaxation times such as T1 value and T2 value to calculate T1 value and T2 value of gray matter in a specific region.

Although the horizontal magnetic field MRI has been described in the above example, the same processing can be applied by using the vertical magnetic field MRI or other apparatus, and the same effect can be obtained. Moreover, similar processing can be applied to any imaging section such as a cross section, a coronal section, a sagittal section, an oblique section, and the like, and similar effects can be obtained.

What is claimed is:

1. An image processor comprising:
   a tissue segmentation processing unit that performs tissue segmentation processing on at least one of a plurality of complex images generated based on a magnetic resonance signal generated from a subject to calculate a tissue image related to a predetermined specific tissue;
   a magnetic susceptibility image calculation unit that calculates a magnetic susceptibility image showing magnetic susceptibility of a predetermined tissue included in the complex image from the complex image;
   an spatially normalization processing unit that calculates a spatially-normalized magnetic susceptibility image and a spatially-normalized tissue image by performing spatially normalization processing on the magnetic susceptibility image and the tissue image and calculates a volume modulated spatially-normalized tissue image obtained by performing volume modulation on the spatially-normalized tissue image;
   a magnetic susceptibility calculation unit that calculates magnetic susceptibility of the specific tissue based on the spatially-normalized magnetic susceptibility image and the spatially-normalized tissue image; and
   a diagnostic index calculation unit that calculates a diagnostic index for diagnosing a predetermined disease based on the magnetic susceptibility of the specific tissue and the volume modulated spatially-normalized tissue image.

2. The image processor according to claim 1, wherein the specific tissue is gray matter.

3. The image processor according to claim 1, wherein the diagnostic index calculation unit calculates a z score as the diagnostic index.

4. The image processor according to claim 1, further comprising:
   a vein removal processing unit that calculates a vein removed magnetic susceptibility image from which a region related to a vein on the magnetic susceptibility image is removed,
   wherein the spatially normalization processing unit performs spatially normalization processing on the vein removed magnetic susceptibility image.

5. The image processor according to claim 4, wherein the vein removal processing unit calculates an individual atlas image, and performs vein removal processing on the magnetic susceptibility image using the individual atlas image.

6. The image processor according to claim 4, wherein the vein removal processing unit calculates the individual atlas image, and performs calcification region removal processing on the magnetic susceptibility image using the individual atlas image.

7. The image processor according to claim 1, wherein the tissue image and the magnetic susceptibility image are calculated based on the same complex image.

8. The image processor according to claim 1, wherein the tissue image and the magnetic susceptibility image are calculated based on different complex images generated from magnetic resonance signals of different echo times.

9. An image processing method comprising:
   a tissue segmentation processing step of performing tissue segmentation processing on at least one of a plurality of complex images generated based on a magnetic resonance signal generated from a subject to calculate a tissue image related to a predetermined specific tissue;
   a magnetic susceptibility image calculation step of calculating a magnetic susceptibility image showing magnetic susceptibility of a predetermined tissue included in the complex image from the complex image;
   an spatially normalization processing step of calculating a spatially-normalized magnetic susceptibility image and a spatially-normalized tissue image by performing spatially normalization processing on the magnetic susceptibility image and the tissue image and calculating a volume modulated spatially-normalized tissue image obtained by performing volume modulation on the spatially-normalized tissue image;
   a magnetic susceptibility calculation step of calculating magnetic susceptibility of the specific tissue based on the spatially-normalized magnetic susceptibility image and the spatially-normalized tissue image; and
   a diagnostic index calculation step of calculating a diagnostic index for diagnosing a predetermined disease based on the magnetic susceptibility of the specific tissue and the volume modulated spatially-normalized tissue image.

10. A program for image processing which causes a computer to execute
    an image processing method comprising:
    a tissue segmentation processing step of performing tissue segmentation processing on at least one of a plurality of complex images generated based on a magnetic resonance signal generated from a subject to calculate a tissue image related to a predetermined specific tissue;
    a magnetic susceptibility image calculation step of calculating a magnetic susceptibility image showing magnetic susceptibility of a predetermined tissue included in the complex image from the complex image;
    an spatially normalization processing step of calculating a spatially-normalized magnetic susceptibility image and a spatially-normalized tissue image by performing spatially normalization processing on the magnetic susceptibility image and the tissue image and calculating a volume modulated spatially-normalized tissue image obtained by performing volume modulation on the spatially-normalized tissue image;
    a magnetic susceptibility calculation step of calculating magnetic susceptibility of the specific tissue based on the spatially-normalized magnetic susceptibility image and the spatially-normalized tissue image; and
    a diagnostic index calculation step of calculating a diagnostic index for diagnosing a predetermined disease based on the magnetic susceptibility of the specific tissue and the volume modulated spatially-normalized tissue image.

11. A magnetic resonance imaging apparatus comprising:
    a measuring unit that measures a magnetic resonance signal generated from a subject by applying a high frequency magnetic field pulse and a gradient magnetic field to the subject placed in a static magnetic field;

an image reconstruction unit that reconstructs an image based on the magnetic resonance signal; and an image processing unit that calculates a diagnostic index for diagnosing a predetermined disease from the image, wherein the image processing unit includes a tissue segmentation processing unit that performs tissue segmentation processing on at least one of a plurality of complex images generated based on the magnetic resonance signal generated from the subject to calculate a tissue image related to a predetermined specific tissue, a magnetic susceptibility image calculation unit that calculates a magnetic susceptibility image showing magnetic susceptibility of a predetermined tissue included in the complex image from the complex image, an spatially normalization processing unit that calculates a spatially-normalized magnetic susceptibility image and a spatially-normalized tissue image by performing spatially normalization processing on the magnetic susceptibility image and the tissue image and calculates a volume modulated spatially-normalized tissue image obtained by performing volume modulation on the spatially-normalized tissue image, a magnetic susceptibility calculation unit that calculates magnetic susceptibility of the specific tissue based on the spatially-normalized magnetic susceptibility image and the spatially-normalized tissue image, and a diagnostic index calculation unit that calculates the diagnostic index for diagnosing the predetermined disease based on the magnetic susceptibility of the specific tissue and the volume modulated spatially-normalized tissue image.

12. The magnetic resonance imaging apparatus according to claim 11, wherein the measuring unit measures at least two magnetic resonance signals having different echo times based on a gradient echo type pulse sequence, and the tissue image and the magnetic susceptibility image are calculated based on different complex images generated from the magnetic resonance signals having the different echo times.

\* \* \* \* \*